United States Patent
Lee et al.

[11] Patent Number: 6,077,409
[45] Date of Patent: Jun. 20, 2000

[54] AIR-TO-FUEL RATIO SENSOR

[75] Inventors: Jong-heun Lee; Kyo-yeol Lee, both of Seoul, Rep. of Korea

[73] Assignee: Samsung Electronics Co., Ltd., Kyungki-do, Rep. of Korea

[21] Appl. No.: 08/897,667

[22] Filed: Jul. 21, 1997

[30] Foreign Application Priority Data

Jul. 19, 1996 [KR] Rep. of Korea ............ 96-29308

[51] Int. Cl.[7] ............................................. G01N 27/407
[52] U.S. Cl. .................... 204/425; 204/426; 204/429; 205/784.5
[58] Field of Search .................................. 204/421–429

[56] References Cited

U.S. PATENT DOCUMENTS

| | | | |
|---|---|---|---|
| 4,304,652 | 12/1981 | Chiba et al. | 204/426 |
| 4,505,806 | 3/1985 | Yamada | 204/426 |
| 4,882,033 | 11/1989 | Shibata et al. | 204/426 |
| 4,961,835 | 10/1990 | Kobayashi et al. | 204/421 |
| 5,130,210 | 7/1992 | Iwasaki et al. | 429/33 |
| 5,419,827 | 5/1995 | Nanataki et al. | 204/421 |
| 5,681,784 | 10/1997 | Friese | 204/421 |

OTHER PUBLICATIONS

Jong–Heun Lee, et al. Sensors and Actuators, Limiting current and wide range etc. 1996 month unavailable, pp. 278–284.

*Primary Examiner*—T. Tung
*Attorney, Agent, or Firm*—Kile, McIntyre, Harbin & Lee; Eugene M. Lee

[57] ABSTRACT

An air-to-fuel (A/F) ratio sensor includes an insulation layer, two solid electrolyte layers made of a porous composite ceramic formed at both sides of the insulation layer, each solid electrolyte layer having an internal electrode layer on its boundary surface with the insulation layer and an external electrode layer on its other surface, and a diffusion barrier layer made of a porous composite ceramic, covering one of the external electrode layers. The A/F ratio sensor provides a linear A/F ratio signal by controlling only a pumping current for a reference partial pressure of oxygen. Thus, the A/F ratio sensor operates by a simpler driving principle, thereby simplifying the driving circuit thereof.

7 Claims, 7 Drawing Sheets

AIR-TO-FUEL RATIO SENSOR

BACKGROUND OF THE INVENTION

1. Field of the Invention

The present invention relates to an air-to-fuel ratio sensor, and more particularly, to an air-to-fuel ratio sensor having durability against thermal shock. The air-to-fuel ratio sensor also is capable of being operated easily by a driving circuit adopting a simple driving principle.

2. Description of Related Art

In an automobile engine, performance, fuel consumption and the amount of exhaust gases change according to the air-to-fuel (A/F) ratio. Thus, it is desirable to set an optimum A/F ratio according to driving conditions.

A majority of gasoline engines employ an oxygen sensor, which typically is called a lambda sensor. The lambda sensor enables gasoline engines to be operated in the stoichiometric point to maximize the efficiency of a 3-way catalyst. This sensor can detect fuel-lean or fuel-rich from the exhaust gas composition. This sensor shows abrupt change of signal, however, at the stoichiometric point. Accordingly, by using the lambda sensor, it is impossible to measure the degree of the A/F deviation from the stoichiometric point.

A lean-burn engine capable of operating at the fuel-lean condition for saving fuels, however, requires a wide-range A/F sensor capable of detecting how much rich or lean the fuel is, as well as whether the fuel is rich or not. Thus, there currently has been significant research into various wide-range A/F ratio sensors.

A wide-range A/F sensor enables detection of whether the fuel is rich or not, and is less dependent on temperature, representing a linear A/F ratio signal in the fuel lean condition.

FIG. 1 is a schematic sectional view showing a conventional wide range A/F ratio sensor. The A/F ratio sensor includes a pumping cell enabling movement of oxygen ions in a desired direction, a sensing cell enabling sensing of electromotive forces according to the difference in partial pressures of oxygen, a diffusion barrier 3 for controlling the diffusion of gas, a cavity 7 enclosed by the diffusion barrier 3, and a dense layer 6 for maintaining the partial pressure of oxygen contacting an air reference electrode 1b of the sensing cell to a predetermined level.

Here, the pumping cell includes a solid electrolyte 4 that is conductive to oxygen ions, and two electrodes 5a and 5b attached to both sides of the solid electrolyte 4 to move oxygen ions via the solid electrolyte 4.

Similarly, the sensing cell includes electrolyte 2 that is conductive to oxygen ions, and two electrodes 1a and 1b attached to both sides of the solid electrolyte 2. The electrodes 1a and 1b are used to measure internal electromotive forces generated by the difference in partial pressures of oxygen.

Also, the diffusion barrier 3 is formed between the sensing cell and the pumping cell, and the cavity 7 is formed between the sensing cell and the pumping cell, and is enclosed by the diffusion barrier 3. The diffusion barrier 3 acts to restrict the flow of the exhaust gas into the electrode 5a and is formed of a material that is not conductive to oxygen ions and electricity in order to prevent interference between the sensing cell and the pumping cell.

The A/F ratio sensor is based on the principle that both the amount and direction of the pumping current for maintaining the partial pressure of oxygen in the cavity 7 change as the partial pressure of oxygen contained in the exhaust changes.

Referring to FIGS. 1, 2 and 3, the driving principles of the conventional A/F ratio sensor will be described in detail.

FIG. 2 is a graph illustrating the principle of sensing oxygen by a general limiting current sensor in the oxidation atmosphere. As shown in FIG. 2, current continuously increases together with an increase in the applied voltage in a section in which the amount of diffused oxygen is increased continuously. However, if the amount of pumped oxygen increases to a predetermined level or more, the diffusion of oxygen itself is limited, so that a predetermined pumping current flows. Here, the amount of oxygen diffused into a cathode is directly proportional to the concentration of oxygen outside the diffusion barrier. Thus, a pumping current proportional to the oxygen concentration can be obtained as a signal for a sensor.

Meanwhile, in a reduction atmosphere, oxygen is pumped to a diffusion barrier from the outside and then reacted with a reduction gas contained in the exhaust gas. Thus, the limiting current becomes proportional to the amount of the diffused reduction gas (FIG. 3).

As can be seen from FIGS. 2 and 3, in the conventional A/F ratio sensor operating by the above principle, the direction of the oxygen ion movement differs depending on whether the fuel is rich or lean. That is, in the fuel lean region, as a voltage Vp is applied to the pumping cell of the A/F ratio sensor, oxygen ions near the electrode 5a move toward the other electrode 5b via the solid electrolyte 4. In a state where the voltage is not applied to the pumping cell, there is scarcely any difference in the oxygen concentration between the electrodes 1a and 1b, so that the electromotive force of the sensing cell is almost zero. In order to maintain the equilibrium partial pressure of the oxygen in the cavity at approximately $10^{-10}$ atm, the electromotive force of the sensing cell should be at approximately 400–450 mV. The wide-range A/F ratio sensor controls the electromotive force of the sensing cell to approximately 400–450 mV through a feedback control of the pumping current by an electrical circuit. The current when the electromotive force of the sensing cell is 400–450 mV corresponds to the limiting currents with regard to oxygen. Therefore, the pumping current in this region is proportional to the equilibrium oxygen concentration in the exhaust gas.

On the other hand, the equilibrium partial pressure of oxygen is very low, i.e., approximately $10^{-20}$ atm in the fuel rich region, and the electromotive force of the cell generated by the difference in partial pressure of oxygen is very high, as much as approximately 900 mV. In order to increase the equilibrium oxygen pressure in the cavity 7 to approximately $10^{-10}$ atm, oxygen should be pumped into the internal electrode 5a from the external electrode 5b. Thus, as in the case where the fuel is lean, the pumping current for maintaining the voltage of the sensing cell at 450 mV through the feedback control is expressed by a signal. As the fuel is richer, there is more reducing gas and the equilibrium partial pressure of oxygen is low. In this case, the magnitude of the pumping current increases. On the electrode 5a, the reduction gas of the exhaust gas, such as carbon monoxide and hydrogen, reacts with oxygen provided via the solid electrolyte 4 to generate carbon dioxide and water.

As described above, in the conventional A/F ratio sensor, the direction of the oxygen ion movement is changed according to whether the fuel is rich or lean. Also, feedback control is required to maintain the equilibrium partial pressure of oxygen in the cavity to a predetermined level. Accordingly, in the conventional A/F ratio sensor, the driving circuit elements are complicated.

Also, in the conventional A/F ratio sensor, the electrolyte layers of the pumping cell and the sensing cell, the porous diffusion barriers and the dense layer for forming the air reference electrode are made of different materials. It is therefore difficult to control the difference of shrinkage during the co-firing of these components. Also, if the sensor is used for a long time at a high temperature, a conventional sensor having these various layers, each made of different materials, will likely become deteriorated by a cyclic thermal shock due to the different thermal expansion of the materials.

SUMMARY OF THE INVENTION

Thus, there exists a need to provide an A/F ratio fuel sensor that does not suffer from these disadvantages. It is therefore an object of the present invention to provide an air-to-fuel (A/F) ratio sensor that has a simplified driving circuit and operation which is achieved by adopting a simple driving principle. It is an additional object of the invention to provide a method of making an air-to-fuel (A/F) ratio sensor having the aforementioned characteristics.

In accordance with these and other objects of the invention, there is provided an A/F ratio sensor comprising an insulation layer, two solid electrolyte layers made of a porous composite ceramic and formed at both sides of the insulation layer. Each solid electrolyte has an internal electrode layer on its boundary surface with the insulation layer, and an external electrode layer on the other boundary surface thereof. The A/F ratio sensor of the invention also includes a diffusion barrier layer made of the porous composite ceramic that covers one of the external electrode layers.

In accordance with an additional object of the invention, there is provided a method of making an A/F ratio sensor, and an A/F ratio sensor made by the process. The process of the invention entails first forming at least three stabilizer-stabilized zirconia-structure modifier (SSZ-SM) green sheets by mixing SSZ and a structure modifier in a predetermined ratio. Then, adding a bonding agent, a plasticizer and a solvent to produce a mixture, milling the mixture, optionally de-gassing the milled mixture to form a slurry, and then forming at least three green sheets from the slurry. Electrode patterns then are formed on two of the at least three green sheets to form first and second electrodes. A third green sheet is attached as a diffusion barrier layer on one side of the first electrolyte, and an insulation layer is attached on the other side of the first electrolyte. The second electrode then is attached to the side of the insulation layer opposite the side in which it is attached to the first electrolyte. The resultant stacked material then is dried and sintered to form an A/F ratio fuel sensor.

BRIEF DESCRIPTION OF THE DRAWINGS

The above objects and advantages of the present invention will become more apparent by describing in detail a preferred embodiment thereof with reference to the attached drawings in which.

DETAILED DESCRIPTION OF THE PREFERRED EMBODIMENTS

An air-to-fuel (A/F ratio) sensor according to the present invention includes an insulation layer, two solid electrolyte layers made of a porous composite ceramic that are formed at both sides of the insulation layer. Each of the two solid electrolyte layers has an internal electrode layer on its boundary surface with the insulation layer and an external electrode layer on its other boundary surface. The A/F ratio sensor also includes a diffusion barrier layer made of the porous composite ceramic, where the diffusion barrier layer covers at least one of the external electrode layers. In the A/F ratio sensor, oxygen ions passing through a solid electrolyte move in the same direction regardless of the A/F ratio, so that a driving circuit thereof can operate easily.

To this end, a material enabling both gas diffusion and ion transfer is used for an electrolyte layer. Any material can be used that is capable of permitting both gas diffusion and ion transfer. Preferably, materials having these characteristics include an SSZ-SM obtained by adding a structure modifier (SM) to a stabilizer-stabilized zirconia (SSZ) (for example, stabilizer is yttria, calcia or magnesia) which is generally used as a solid electrolyte. Here, as the structure modifier for modifying fine structures of a diffusion barrier layer and an electrolyte layer, an insulator such as alumina or magnesium oxide, or a solid electrolyte such as Yttria Stabilized Zirconia (YSZ), Calcia Stabilized Zirconia (CSZ) or Magnesia Stabilized Zirconia (MSZ) may be used. Preferably, the particle size of the structure modifier is different from that of the SSZ powder.

The insulation layer may be formed of general insulation materials used for the A/F ratio sensor. Preferably, these materials can include alumina or mullite ($3Al_2O_3 \cdot 2SiO_2$).

Figure 1:
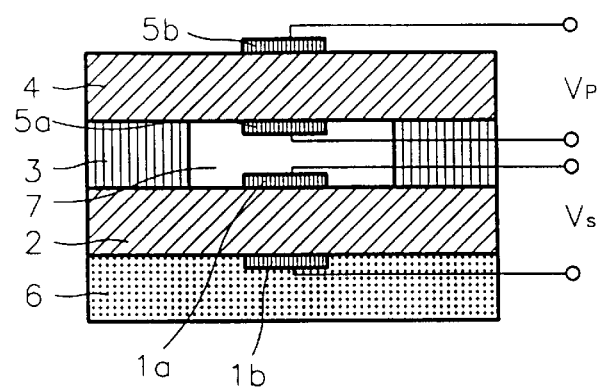
FIG. 1 is a schematic section view of a conventional wide range air-to-fuel (A/F) ratio sensor.
Figure 2:
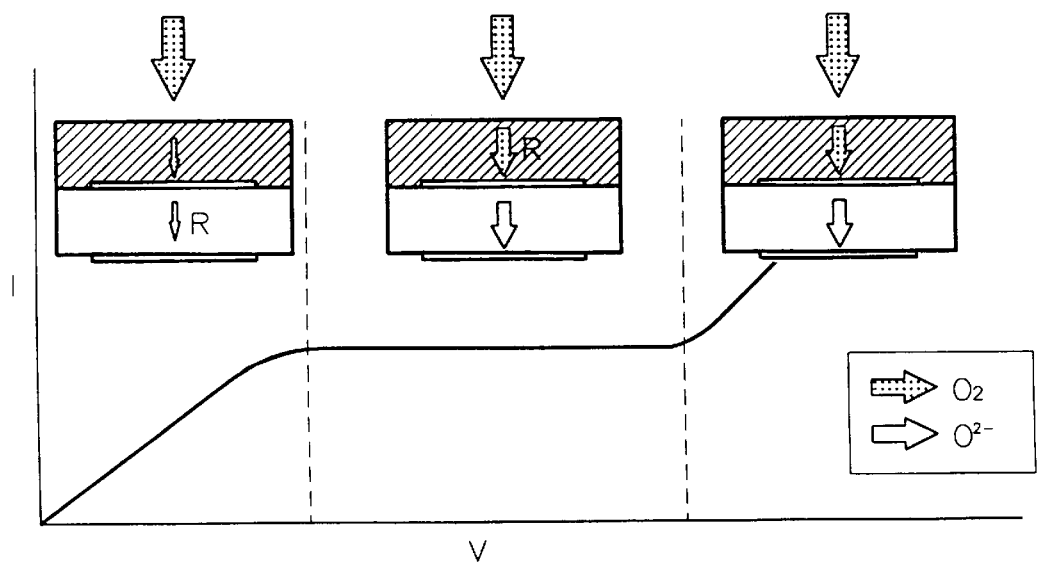
FIG. 2 is a graph illustrating the principle of sensing oxygen in an oxidation atmosphere by a general limiting current sensor.
Figure 3:
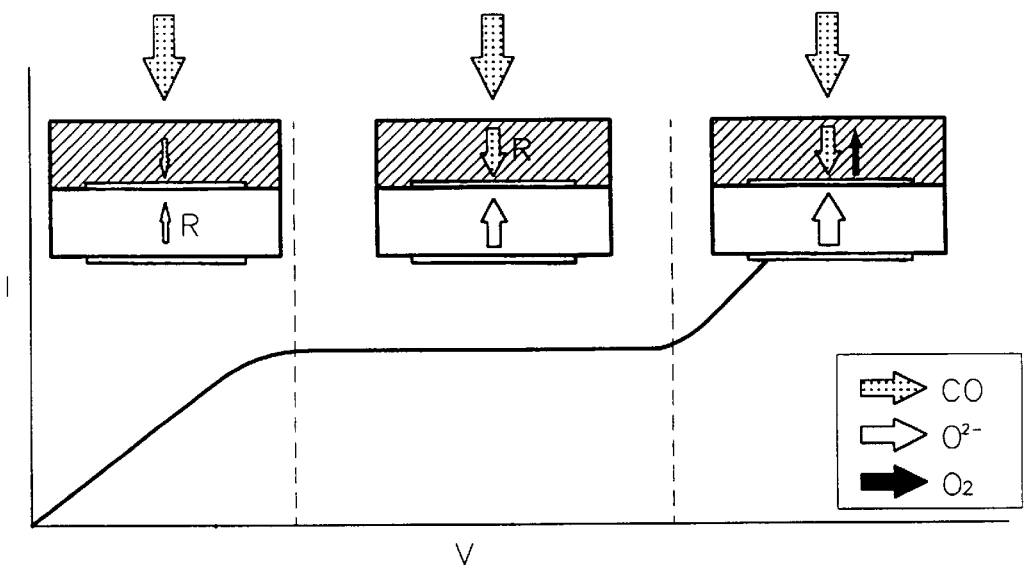
FIG. 3 is a graph illustrating the principle of sensing carbon monoxide in a reduction atmosphere by a general limiting current sensor.
Figure 4:
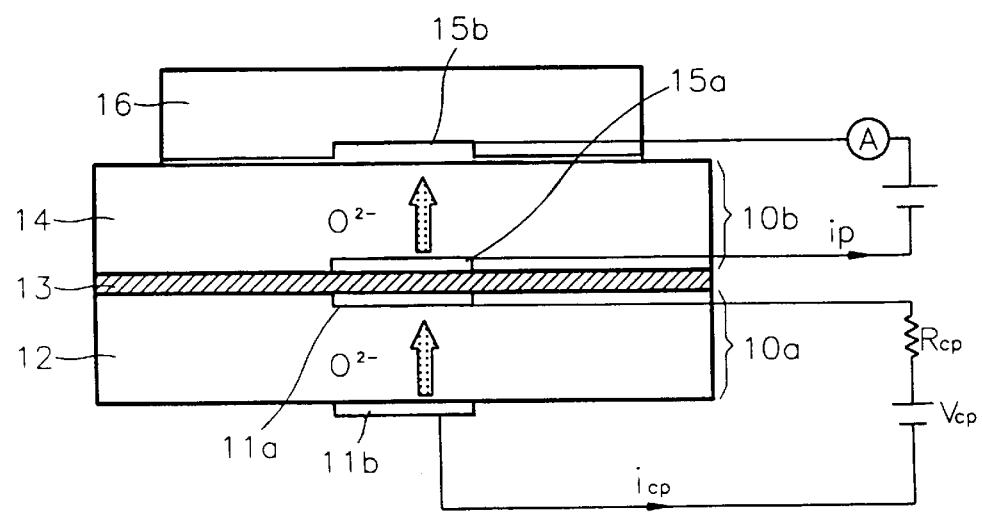
FIG. 4 is a schematic section view of an A/F ratio sensor according to a preferred embodiment of the present invention.

FIG. 4 is a schematic section view of an A/F ratio sensor according to a preferred embodiment of the present invention. The A/F ratio sensor includes first cell 10a including two electrodes 11a and 11b at both sides of an electrolyte layer 12, second cell 10b having two electrodes 15a and 15b at both sides of an electrolyte layer 14, an electrical insulation layer 13 interposed between the first and second cells 10a and 10b, and a diffusion control barrier 16 covering the external electrode 15b of the second cell 10b. Referring to FIG. 4, the operating principle of the A/F ratio sensor of the present invention will be described according to whether the fuel is rich or lean, and an oxygen pumping amount of cell 10a ($I_{cp}$) is equal to 0 or not, that is $I_{cp}$ is equal to 0 or not.

First, when $I_{cp}=0$, i.e., $V_{cp}=0$, the A/F ratio sensor operates as follows. The term $V_{cp}$ denotes the voltage applied to cell 10a to keep the oxygen partial pressure at a predetermined level near the electrode 11a. The term $I_{cp}$ refers to the current applied to cell 1a by voltage $V_{cp}$.

Figure 5:
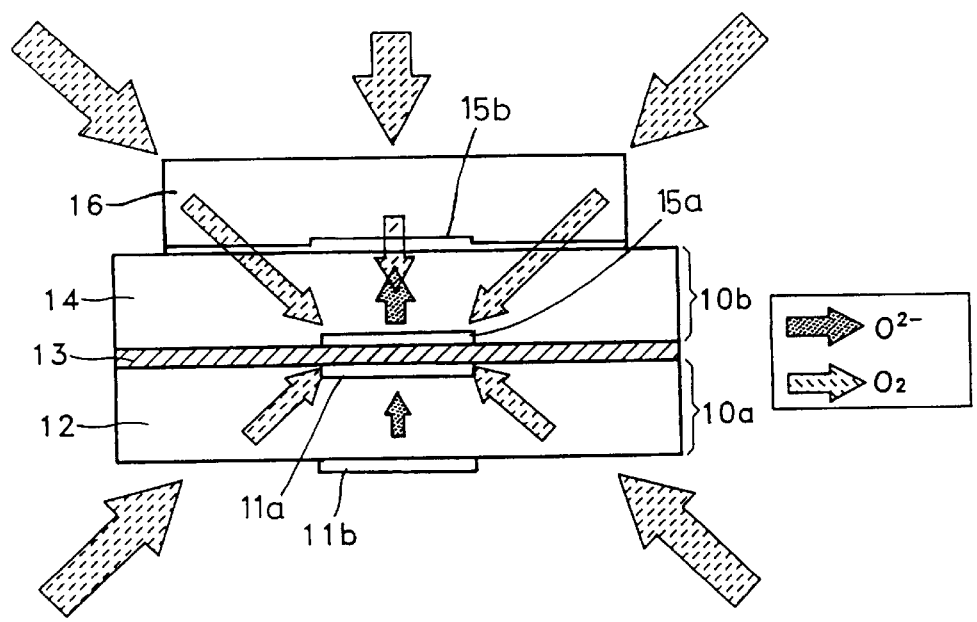
FIG. 5 is a diagram illustrating the operation of the A/F sensor according to the present invention in a fuel lean region.

In an oxidation atmosphere where the fuel is lean, as shown in FIG. 5, when the voltage of the second cell 10b increases gradually, the amount of oxygen pumped from the electrode 15a to the electrode 15b increases gradually. Since porous electrolyte-SM composites 12, 14 and 16, and the insulation layer 13 act as a gas diffusion barrier, the amount of oxygen pumped from the electrode 15a to the electrode 15b is determined by the diffusion of oxygen from all parts of the sensor toward the electrode 15a when the oxygen concentration at the electrode 15a decreases. Thus, the limiting current value which is proportional to the oxygen concentration can be measured.

Figure 6:
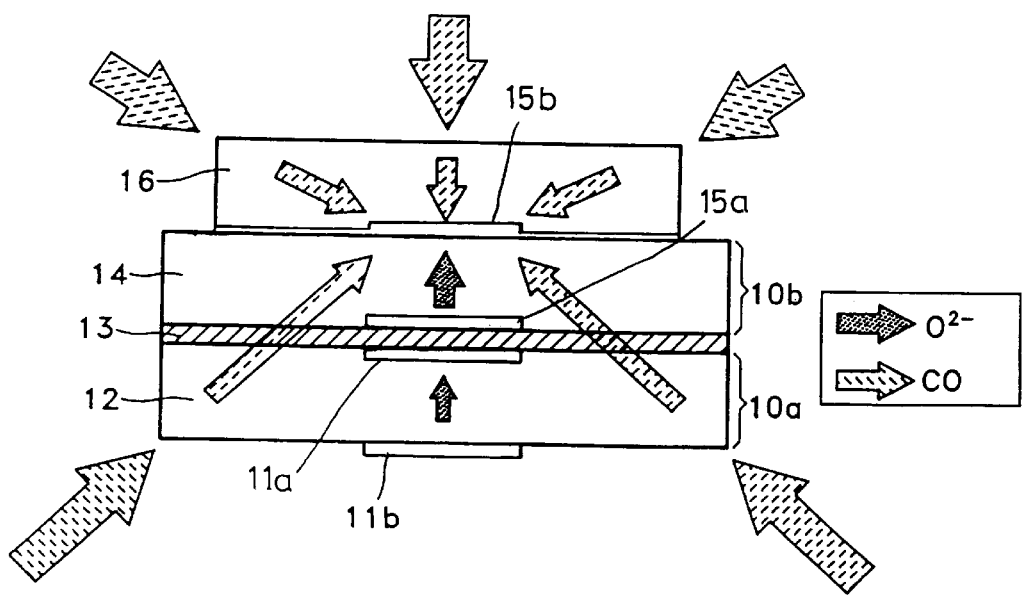
FIG. 6 is a diagram illustrating the operation of the A/F sensor according to the present invention in a fuel rich region.

Meanwhile, in a reduction atmosphere where the fuel is rich, as shown in FIG. 6, when the voltage of the second cell 10b increases gradually, the amount of oxygen pumped from the electrode 15a to the electrode 15b increases gradually. Here, the amount of oxygen consumed at the electrode 15b determines the amount of oxygen to be pumped. Also, since the porous electrolyte-SM composites 12, 14 and 16, and the insulation layer 13 act as a gas diffusion barrier, the amount of oxygen pumped from the electrode 15a to the electrode 15b is determined by the amount of a reduction gas diffused from all parts of the sensor to the electrode 15b when the oxygen concentration of the electrode 15b increases. Thus, the limiting current value is proportional to the concentration of reduction gas such as CO, HC or $H_2$.

Thus, in the A/F ratio sensor of the present invention, the limiting current which is proportional to the concentration of oxygen in the fuel-lean condition, and the limiting current which is proportional to the concentration of the reduction gas in the fuel-rich condition can be measured. However, in the state where $I_{cp}=0$, the direction of the pumping current in the fuel-lean condition is the same as that in the fuel-rich condition, so that it is impossible to determine whether the fuel is lean or rich by using the limiting current. Therefore, the $I_{cp}$ is introduced to determine whether the fuel is fuel-lean or fuel-rich.

Second, when $I_{cp}$ is not equal to 0, i.e., $V_{cp} \neq 0$, the A/F ratio sensor operates as follows.

When the voltage $V_{cp}$ is applied to the first cell 10a, the oxygen molecule is changed into ions at the electrode 11b which then can pass through the solid electrolyte 12. The oxygen ions which pass through the solid electrolyte 12 then are oxidized at the electrode 11a and changed back into the oxygen molecules. This oxygen pumping from the electrode 11b to the electrode 11a increases the oxygen partial pressure voltage of the electrode 11a and the electrode 15a. Also, a resistor serially connected to the first cell 10a denotes as $R_{cp}$ in FIG. 4 can be used to minimize the change of the oxygen concentration at the electrodes 11a and 15a (see FIG. 4) which depends on the fuel-lean or fuel-rich.

The fact that the oxygen concentration at the electrodes 11a and 15a increases together with the increase of the $I_{cp}$ means that the limiting current value increases in the oxidation atmosphere. Also, the increase of the oxygen concentrations at the electrodes 11a and 15a under the reduction atmosphere increases the equilibrium partial pressure of oxygen at the electrode 15b by the diffusion of oxygen. Therefore, the sensor can detect or feel the more oxidizing atmosphere, in comparison to the case without $I_{cp}$. As the $I_{cp}$ increases, the limiting current decreases initially. This is because the oxygen concentration at the electrode 15b increases together with the $I_{cp}$ thus lowering the concentration of the reduction gas. However, if the $I_{cp}$ further increases, the condition of the electrode 15b is changed into an oxidation atmosphere, so that the limiting current increases.

If a predetermined magnitude of $I_{cp}$ is applied to the first cell 10a using the above phenomenon, the limiting current at the oxidation atmosphere further increases while the limiting current at the reduction atmosphere decreases. As a result, the limiting current at the oxidation atmosphere can be obtained as a sensor signal without the need for a complicated circuit for the feedback control of the wide-range A/F ratio.

As described above, in the A/F ratio sensor of the present invention, $I_{cp}$ is set to a predetermined value or more in the fuel-rich (reduction) and fuel-lean (oxidation) atmospheres to express the magnitude of limiting current by a monotonous increasing value. The limiting current can be obtained as a linear signal. Accordingly, if $I_{cp}$ is maintained at a predetermined value or more, current detected at a predetermined voltage is in linear proportion to the A/F ratio.

Hereinafter, a process for manufacturing the A/F ratio sensor according to the present invention will be described.

First, stabilizer-stabilized zirconia (SSZ) having an average particle diameter of 0.01~0.1 μm and a structure modifier having average particle diameter of 0.5~5 μm are mixed in a predetermined ratio. A general bonding agent and plasticizer then can be added to the mixture, and a solvent added to the resulting mixture. Ball-milling then can be performed on the resultant mixture. Bubbles preferably are removed through a degassing process to prepare a slurry. Thereafter, a green sheet having a predetermined thickness, e.g., 0.3~1.2 mm, is obtained by using the slurry.

In the present invention, the mixing ratio of the SSZ and the structure modifier can vary different depending on the types of the structure modifiers. First, when an insulating material such as alumina or magnesium oxide is used as the structure modifier, SSZ and the structure modifier preferably are mixed in a ratio of 90:10~70:30 based on weight. This mixing ratio can be determined by considering the fact that if the structure modifier is used in less than the above range, the amount of diffused oxygen will be much less, thereby decreasing the oxygen sensing ability. Alternatively, if the structure modifier exceeds the above range, ionic conductivity of the electrolyte layer will be decreased even though the amount of diffused oxygen increases. However, if an ionic conductive material such as CSZ, YSZ or MSZ is used for the structure modifier, the content of the structure modifier does not affect the ionic conductivity of the electrolyte layer. Thus, there is no limitation in the content of the structure modifier. Those skilled in the art are capable of utilizing a suitable SSZ/structure modifier ratio using the guidelines provided herein.

Materials that are typically used for conventional A/F sensors may be used as a bonding agent and plasticizer. Preferably, polyvinylbutyral (PVB) or polyvinylacetate (PVA) is used as the bonding agent, and butylbenzylphatlate (BBP) or dioctylphtalate (DOP) is used as the plasticizer.

Upon forming the green sheets as mentioned above, first and secondary green sheets each having electrode patterns on both surfaces thereof formed by a conventional method can be prepared. Any method can be used to form the electrode pattern, and skilled artisans are capable of forming the electrode pattern, given the green sheet above. A green sheet for a diffusion barrier then is stacked on one side of the first green sheet, and an insulation layer is attached on the other side of the first green sheet. Then, the secondary green sheet is attached on the insulation layer. Drying and sintering processes then can be performed sequentially on the resultant structure, thereby completing the A/F ratio sensor according to the present invention. Preferably, the sintering is performed at 1,400~1,525° C. for 0.2~4 hours.

According to the present invention, the diffusion barrier layer and the solid electrolyte layer can be formed of the same composition. Thus, there is no need to worry about fine cracks which may occur during the sintering process. In a conventional A/F ratio sensor, the sensor structure may be bent or broken, or cracks may occur at the diffusion barrier during the sintering of the green sheet due to a difference in the heat shrinkage of the diffusion barrier layer and the solid electrolyte layer. These problems are overcome, however, by the present invention.

Hereinafter, examples of the present invention will be described in detail, however, the present invention is not limited to the particular forms to be illustrated.

EXAMPLE 1

A bonding agent comprised of PVB (16 g), 12 g of a plasticizer (DOP), 85 g of yttria-stabilized zirconia (YSZ) powder having an average particle size of 0.05 μm, and 15 g of alumina powder having an average particle size of 1 μm were added to a mixed solvent of toluene and ethanol, and mixed by a ball miller, and then air was removed from the mixture to prepare a slurry. Using this slurry, two green sheets having thicknesses of 0.75 mm (first and second green sheets, respectively) and one green sheet having a thickness of 0.25 mm (third green sheet) were manufactured by a doctor-blade method.

Thereafter, a platinum (Pt) paste was attached to both sides of the first and second green sheets by a screen printing method. Then, each of the resultant platinum pastes was dried at 60° C. for 3 hours to form an electrode, and the above steps were repeated to obtain both electrodes. After stacking the third green sheet on one side of the first green sheet having the electrodes, drying was performed at 60° C. for 3 hours. Then, an alumina layer of 50 μm thickness was formed on the other side of the first green sheet. Subsequently, the second green sheet was stacked on the alumina layer, and then sintering was performed at 1,450° C. for 2 hours in atmospheric conditions.

EXAMPLE 2

Figure 7:
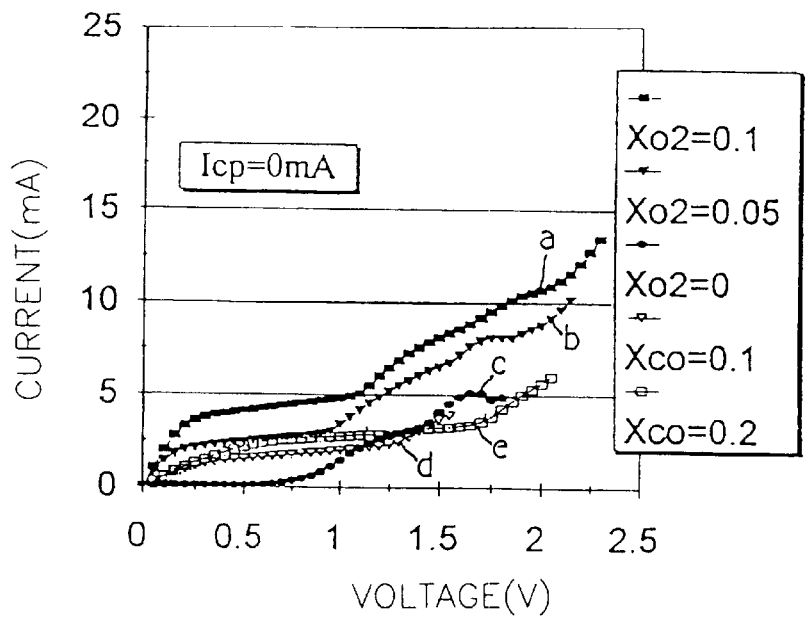
FIGS. 7 through 12 are graphs illustrating the current-to-voltage characteristic according to $I_{cp}$ and the concentration of oxygen or carbon monoxide.
Figure 8:
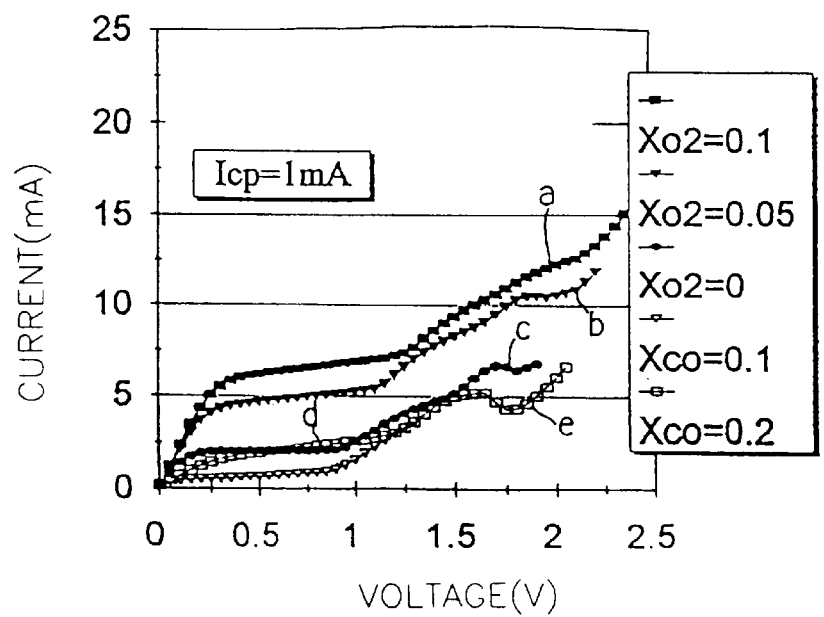
Figure 9:
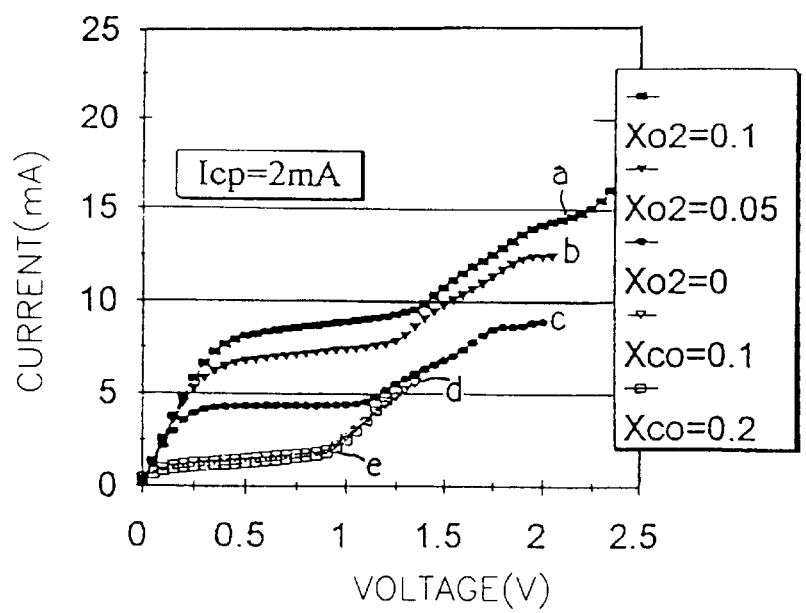
Figure 10:
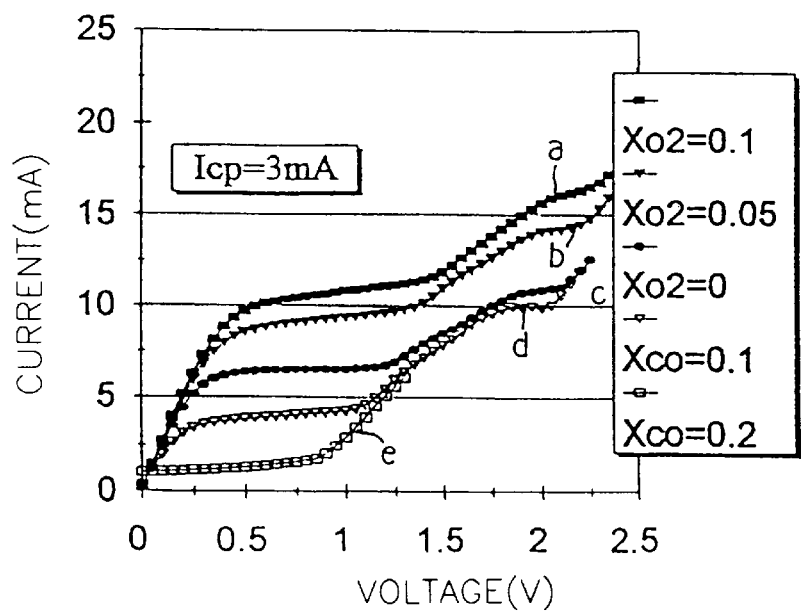
Figure 11:
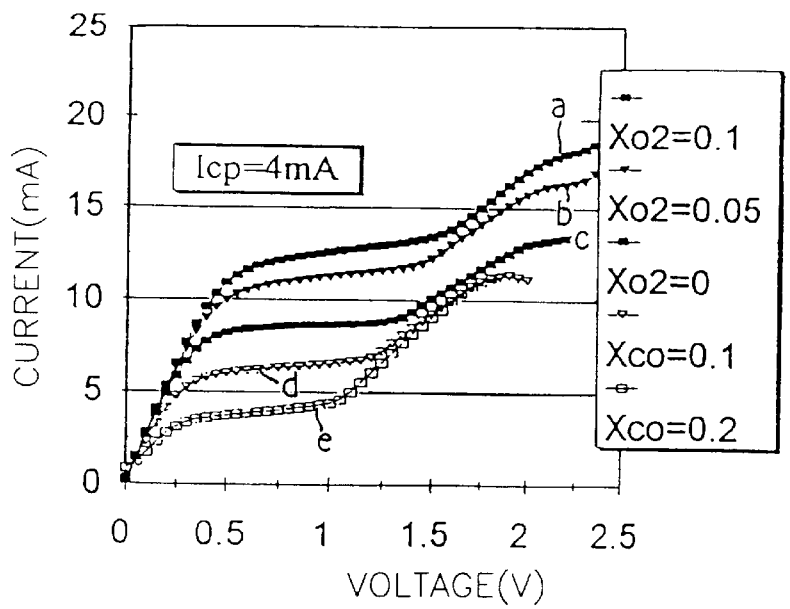
Figure 12:
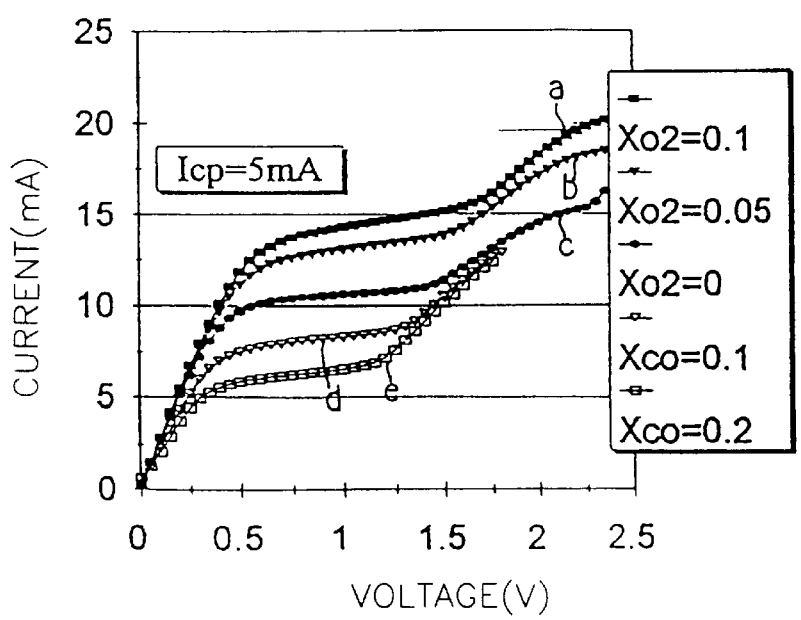

In order to test the oxygen sensing ability of the A/F ratio sensor manufactured in Example 1, the current-to-voltage characteristic was measured according to the concentration of oxygen or carbon monoxide. The results are shown in FIG. 7. Here, the temperature of the sensor was 800° C., $I_{cp}$ was 0 mA, and the total pressure of the gas mixture was fixed to 1 atm. In FIG. 7 "a" represents the current-to-voltage characteristic of a gas mixture having a partial pressure of oxygen ($Xo_2$) of 0.1, "b" represents that of a gas mixture having $Xo_2$ of 0.05, "c" represents that of a gas mixture without oxygen or carbon dioxide, "d" represents that of a gas mixture having a partial pressure of carbon monoxide (Xco) of 0.1, and "e" represents that of a gas mixture having Xco of 0.2. Here, in all of the gas mixtures "a" through "e", the partial pressure of carbon dioxide was 0.2, and the balance was nitrogen.

From FIG. 7, it can be seen that the limiting current amount increases by the increase in oxygen concentration when the fuel is lean ($Xo_2$=0.1 and 0.05), and increases by the increase in carbon monoxide concentration when the fuel is rich (Xco=0.1, 0.2).

EXAMPLE 3

The current-to-voltage characteristic was measured by the same method as that of Example 2, except $I_{cp}$ was set to 1 mA, 2 mA, 3 mA, 4 mA and 5 mA, respectively. The results are shown in FIGS. 8 through 12, respectively. In FIGS. 8 through 12, "a" through "e" represent the same gas mixtures as those of Example 2. As can be seen from FIGS. 7–12, as $I_{cp}$ increases, the limiting current at the oxidation atmosphere increases, while the limiting current at the reduction atmosphere decreases initially and then increases. In other words, with $I_{cp}$ increasing from 0 to 2 mA, limiting current in oxidizing atmosphere increases and that in reducing atmosphere decreases. However, with the $I_{cp}$ being 3 mA or higher value, the monotonous and linear sensor signal can be attained.

Figure 13:
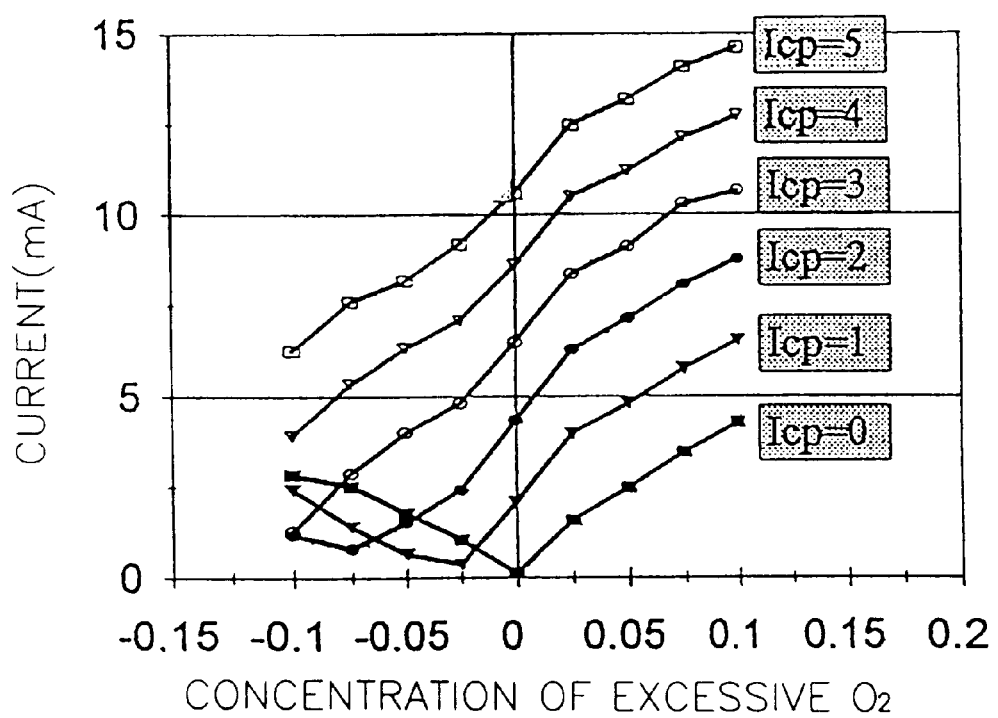
FIG. 13 is a graph showing the limiting current as a function of the concentration of oxygen or carbon monoxide under variable $I_{cp}S$.

The limiting current of FIGS. 7–12 is shown in FIG. 13 according to the concentration of gas. In FIG. 13, the right half represents the oxidation (fuel-lean) atmosphere, and the left half represent the reduction (fuel-rich) atmosphere. At $I_{cp}$=0, the limiting current curve is bent as a V-shape near the theoretical A/F ratio. Also, it can be seen that the minimum current point moves toward the reduction atmosphere side as $I_{cp}$ increases to 2 mA. This is because the concentration of the reducing gas decreases at the electrodes 15a and 15b by the oxygen pumping from the electrode 11b to the electrode 11a.

If $I_{cp}$ further increases, the V-shaped curve is linearized. This means that the reduction atmosphere of the electrode 15b is changed into the oxidation atmosphere by the oxygen pumping from electrode 11b to electrode 11a. Thus, if $I_{cp}$ set to a predetermined level or more, the linear limiting current value which monotonously increases over a whole region from a low A/F ratio region (e.g., fuel rich region) to a high A/F ratio region (e.g., fuel-lean region) can be obtained.

As described above, the A/F ratio sensor of the present invention can provide a linear A/F ratio signal by only controlling a pumping current for a reference partial pressure of oxygen, and the magnitude of current obtained as a signal can be controlled. Thus, the A/F ratio sensor of the present invention adopts a simpler driving principle than that of the conventional A/F sensor, so that the driving circuit thereof can be simplified.

In addition, the diffusion barrier layer and the electrolyte layer, both of which are composed of the same material, i.e., SSZ-SM, have the same or similar heat shrinkage. Thus, the problem of cracking during a sintering process can be solved. Also, the electrolyte and the diffusion barrier are formed of the same material, so that there is no deterioration caused by the different heat expansion ratios when the sensor is used for a long time.

The invention has been described with reference to particularly preferred embodiments and examples. Those skilled in the art will appreciate, however, that various modifications can be made to the invention without significantly departing from the spirit and scope thereof. All documents referred to herein are incorporated by reference in their entirety. Korean Patent Application Number 96-29308, filed Jul. 19, 1996, is incorporated herein by reference.

What is claimed is:

1. An air-to-fuel (A/F) ratio sensor comprising:
   an insulating layer;
   a first electrolyte layer over a first side of the insulating layer;
   a second electrolyte layer over a second side of the insulating layer;
   a first electrode over a first side of the first electrolyte layer;
   a diffusion barrier layer over the first electrode;

a second electrode over a second side of the first electrolyte layer;

a third electrode over a first side of the second electrolyte layer;

a fourth electrode over a second side of the second electrolyte layer, and means for generating a first current, $I_{cp}$, between the third and fourth electrodes such that a limiting current between the first and second electrodes increases as the air-to-fuel ratio of an exhaust gas incident on the sensor increases from a fuel rich ratio to a fuel lean ratio, wherein the first and second electrolyte layers over two sides of the insulating layer comprises a composite ceramic made from a stabilizer-stabilized zirconia (SSZ) and a structure modifier having an average particle size larger than the SSZ average particle size.

2. The air-to-fuel (A/F) ratio sensor of claim 1, wherein the diffusion barrier layer is made from the same composite ceramic as the first and second electrolyte layers.

3. The air-to-fuel (A/F) ratio sensor of claim 1, wherein the insulating layer comprises at least one selected from the group consisting of alumina and mullite.

4. The air-to-fuel (A/F) ratio sensor of claim 1, wherein an average particle size of the stabilizer-stabilized zirconia (SSZ) is 0.01–0.1 µm.

5. The air-to-fuel (A/F) ratio sensor of claim 1, wherein the SSZ is at least one selected from the group consisting of yttria stabilized zirconia, calcia stabilized zirconia and magnesia stabilized zirconia.

6. The air-to-fuel (A/F) ratio sensor of claim 1, wherein the structure modifier comprises alumina, magnesium oxide, yttria stabilized zirconia, calcia stabilized zirconia and magnesia stabilized zirconia.

7. The air-to-fuel (A/F) ratio sensor of claim 1, wherein the SSZ and the structure modifier are contained in a ratio of 90:10–70:30 based on weight.

* * * * *